(12) United States Patent
Jongen

(10) Patent No.: US 9,093,209 B2
(45) Date of Patent: Jul. 28, 2015

(54) MAGNET STRUCTURE FOR AN ISOCHRONOUS SUPERCONDUCTING COMPACT CYCLOTRON

(71) Applicant: Ion Beam Applications S.A., Louvain-la-Neuve (BE)

(72) Inventor: Yves Jongen, Louvain-la-Neuve (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 0 days.

(21) Appl. No.: 14/376,100

(22) PCT Filed: Feb. 1, 2013

(86) PCT No.: PCT/EP2013/052104
§ 371 (c)(1),
(2) Date: Jul. 31, 2014

(87) PCT Pub. No.: WO2013/113913
PCT Pub. Date: Aug. 8, 2013

(65) Prior Publication Data
US 2014/0371076 A1 Dec. 18, 2014

(30) Foreign Application Priority Data

Feb. 3, 2012 (EP) .................................. 12153944
Feb. 29, 2012 (EP) .................................. 12157521

(51) Int. Cl.
*H01F 6/02* (2006.01)
*H05H 13/00* (2006.01)
*H01F 6/06* (2006.01)
*H05H 7/04* (2006.01)
*A61N 5/10* (2006.01)

(52) U.S. Cl.
CPC ................ *H01F 6/06* (2013.01); *A61N 5/1077* (2013.01); *H05H 7/04* (2013.01); *H05H 13/005* (2013.01); *H05H 2007/043* (2013.01)

(58) Field of Classification Search
CPC ............... H01F 6/06; H01F 6/00; H01F 6/02; H01F 41/048
See application file for complete search history.

(56) References Cited

U.S. PATENT DOCUMENTS 6,683,426 B1 * 1/2004 Kleeven ......................... 315/502
8,558,485 B2 * 10/2013 Antaya ......................... 315/502
(Continued)

FOREIGN PATENT DOCUMENTS

EP 1069809 A1 1/2001

OTHER PUBLICATIONS

Kawaguchi, Takeo et al., "Design Study of Sector Magnet for the RIKEN Superconducting Ring Cyclotron (2)." EPAC96. Fifth European Particle Accelerator Conference Institute of Physics Publishing Bristol, United Kingdom, vol. 3, 1997, p. 2305.
(Continued)

*Primary Examiner* — Colleen Dunn
(74) *Attorney, Agent, or Firm* — Fitch, Even, Tabin & Flannery LLP

(57) ABSTRACT

The invention relates to a magnet structure for a superconducting isochronous cyclotron for use in particle therapy. The cyclotron according to the invention is using two sets of three or more superconducting sector coil elements for generating an azimuthally varying magnetic field across the acceleration region. In this way, high-field (e.g. above 4 T) isochronous cyclotrons are provided which do not suffer the problem of a low flutter amplitude.

25 Claims, 7 Drawing Sheets

(56) References Cited

U.S. PATENT DOCUMENTS 8,614,612 B2 * 12/2013 Antaya et al. ............... 335/216
8,637,833 B2 * 1/2014 Balakin ..................... 250/396 R
8,933,651 B2 * 1/2015 Balakin et al. ............. 315/503

OTHER PUBLICATIONS

Klein, et al., "Design, Manufacturing and Commissioning of Compact Superconducting 250 MeV Cyclotrons for Proton Therapy: A Short Report from the Field." IEEE/CSC & ESAS European Superconductivity News Forum, No. 2, Oct. 2007, 6 pages.

Mandrillon, P., et al., "A Compact Facility for High Energy Proton Therapy Based on a Superconducting Cyclotron." EPAC, 1994, pp. 2604-2606.
Mitsumoto, T. et al., "Design Study of Sector Magnet for the RIKEN Superconducting Ring Cyclotron (1)." EPAC96. Fifth European Particle Accelerator Conference Institute of Physics Publishing Bristol, United Kingdom, vol. 3, 1997, p. 2302.
Trinks, U. et al., "A prototype coil for the superconducting separated sector cyclotron SuSe." Journal De Physique Colloque France, vol. 45, No. C-1, Jan. 1984, pp. 217-220.
International Search Report and Written Opinion, International Patent Application No. PCT/EP2013/052104, dated Nov. 4, 2013, 13 pages.

* cited by examiner

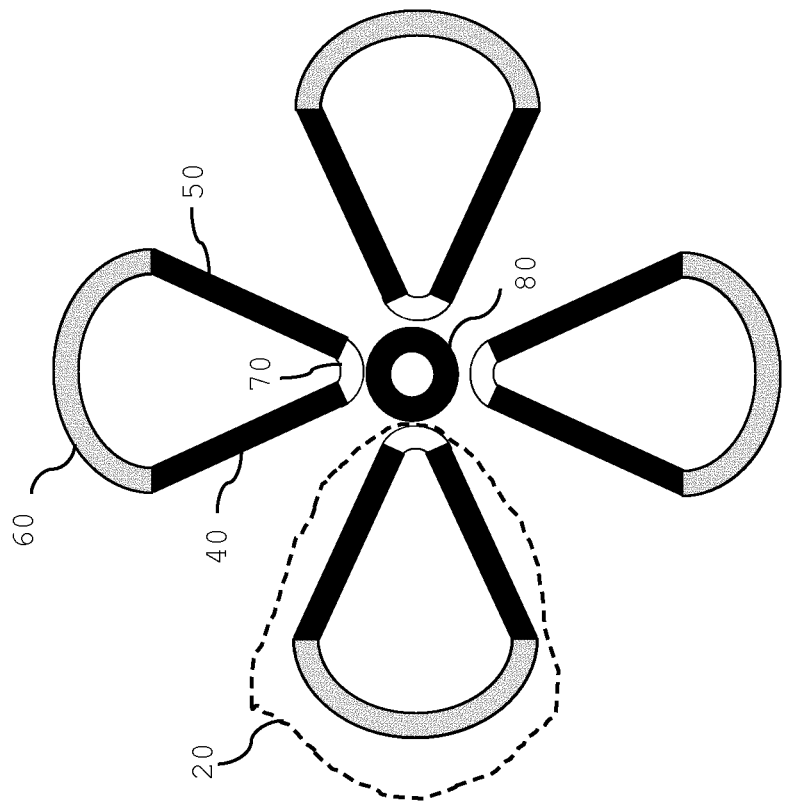
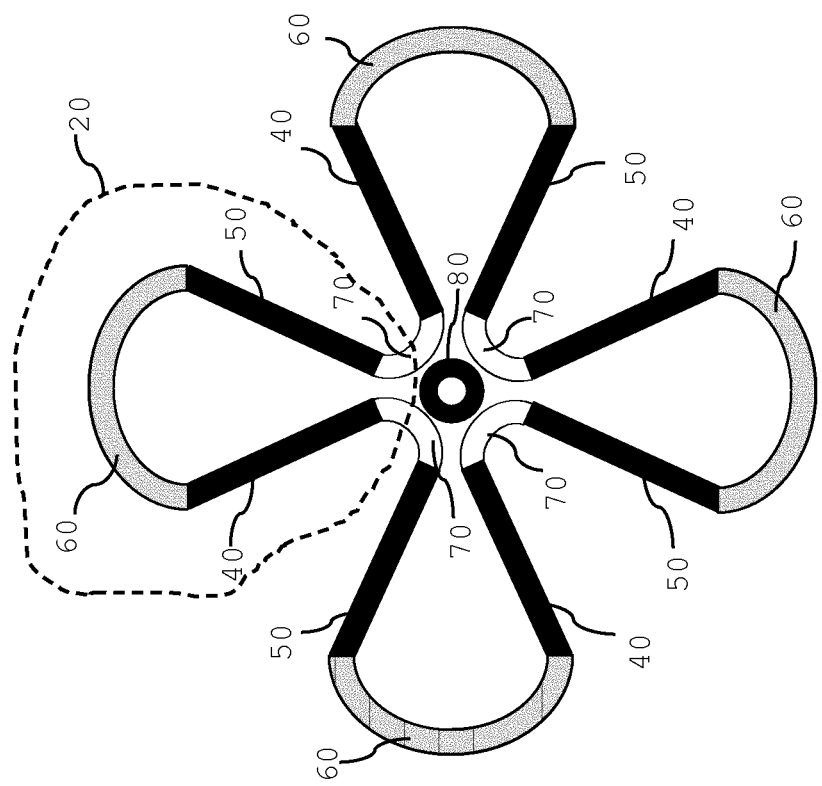
Fig. 7a
Fig. 7b

MAGNET STRUCTURE FOR AN ISOCHRONOUS SUPERCONDUCTING COMPACT CYCLOTRON

CROSS REFERENCE TO RELATED APPLICATIONS

This is a U.S. national phase application of International Application No. PCT/EP2013/052,104, filed Feb. 1, 2013, designating the United States and claiming priority to European Patent Application No. 12/153,944.9, filed Feb. 3, 2012, and European Patent Application No. 12/157,521.1, filed Feb. 29, 2012, which are incorporated herein by reference in their entireties.

FIELD OF THE INVENTION

The field of invention relates to a magnet structure for an isochronous compact cyclotron for accelerating charged particles in an acceleration region. The magnetic structure generates a magnetic field across an acceleration region and this magnetic field is perpendicular to a median plane of the acceleration region. A magnetic structure comprises
 a superconducting coil assembly,
 a ferro-magnetic assembly for guiding a magnetic flux,
 and a cavity forming said acceleration region.

More particularly, the field of invention relates to a compact isochronous superconducting cyclotron for use in particle therapy. For example, for proton therapy, energies up to 250 MeV are preferably required.

DESCRIPTION OF PRIOR ART

Compact isochronous superconducting cyclotrons with a magnetic structure that combines a superconducting coil assembly with a ferro-magnetic assembly are known. Such a ferro-magnetic assembly, generally made out of iron, can comprise various portions such as an upper and a lower pole and/or a return yoke. The superconducting coil assembly consists of one or two annular superconducting coils installed around the acceleration region. The combination of such a superconducting coil assembly with a ferro-magnetic assembly has resulted in the construction of a class of so-called compact isochronous superconducting cyclotrons. The magnetic structure for a cyclotron also has a cavity (i.e. an opening or an area or a gap) forming the acceleration region.

For example, an isochronous superconducting cyclotron for proton therapy is known from Klein et al., in "Design, manufacturing and commissioning of compact 250 MeV Cyclotrons for Proton Therapy: a short report from the field", IEE/CSC & ESAS European superconductivity news forum, No 2, October 2007.

As a superconducting coil assembly, this accelerator described by Klein et al. is using an annular superconducting coil inducing a magnetic field from 2.4 T (Tesla) at the centre of the accelerator and increasing up to about 3 T at the extraction radius. The ferro-magnetic assembly of this accelerator comprises upper and lower iron poles which are saturated by the field of the superconducting coils. As shown in FIG. 2 of this prior art document, the poles have a four sector structure. This pole shape, with hills and valleys, is necessary to focus the beam vertically. It is well known that due to the transitions from hills to valleys the beam will experience focussing kicks and the strength of the focussing depends on the magnitude of the change in field strength between the hills and the valleys. A parameter characterising this ratio of the field strength at the valleys and the hills of the poles is the so-called flutter amplitude. If the flutter amplitude is too low, no stable beam can be generated. The ferro-magnetic assembly of this accelerator further comprises a circular return yoke surrounding the superconducting coils as shown in FIG. 1 of this prior art document.

Another example of a design for an isochronous compact superconducting cyclotron for proton therapy was proposed by P. Mandrillon et al. in "A compact facility for high energy proton therapy based on a superconducting cyclotron", EPAC, 1994. This accelerator is designed for 238 MeV protons and the accelerator comprises three pole sectors and the geometry of the poles is optimized for enhancing the focussing properties. In this accelerator the maximum average magnetic field is about 3 T.

When designing compact superconducting cyclotrons, the external size of the accelerator can be reduced by further increasing the magnetic field strength. However, for isochronous cyclotrons there is a fundamental limitation due to the fact that when further increasing the magnetic field strength, e.g. above 4 T, the relative contribution to the total magnetic field strength originating from the iron poles of the accelerator becomes small. Indeed, the maximum contribution of the iron poles at saturation is about 2 T. The consequence of this is that the flutter amplitude is too small and the beam blows up before it can be extracted. Hence, designs for isochronous superconducting cyclotrons for 250 MeV protons are currently limited to an average field strength of about 4 T resulting in an outer diameter of about 3.2 m.

Due to these limitations of isochronous superconducting cyclotrons, the use of high-field synchrocyclotrons have been proposed in order to build more compact accelerators. As these type of accelerators are not isochronous, they do not suffer from the problems resulting from a radially increasing magnetic field as present in an isochronous cyclotron. On the other hand, synchrocyclotrons are more complex as they require a modulated RF system. An isochronous cyclotron has the advantage to deliver a continuous beam in contrast to a synchrocyclotron where the beam is bunched.

For completeness, a special class of isochronous cyclotrons exists, namely the separated-sector cyclotrons. However, this special class of cyclotrons does, by definition, not belong to the class of compact cyclotrons. Indeed, those separated-sector cyclotrons do not have any iron between the valleys or sectors resulting in a cyclotron with an open structure having large dimensions.

SUMMARY OF THE INVENTION

It is an object of the invention to develop a compact superconducting isochronous cyclotron for use in particle therapy that overcomes the aforementioned limitations of the known compact superconducting isochronous cyclotrons.

In particular, by solving the limitations discussed, higher field isochronous superconducting cyclotrons, resulting in more compact cyclotrons, can be built. The compactness of the accelerator for use in particle therapy is an important factor as it influences the size of the room needed in the hospital or building. The weight is also strongly reduced by reducing the size and hence it becomes easier to handle and is finally also cheaper.

The present invention relates to a magnet structure for an isochronous compact cyclotron for accelerating charged particles, configured for generating a magnetic field across an acceleration region, the magnetic field being perpendicular to a median plane of the acceleration region.

A magnet structure for a compact superconducting cyclotron is generally comprising a superconducting coil assembly, a ferro-magnetic assembly for guiding a magnetic flux and a cavity forming the acceleration region.

The magnetic structure according to the invention is comprising a series of three or more superconducting sector coil elements located on top and below said acceleration region, said sector coil elements being configured for varying azimuthally said magnetic field between a lower magnetic field value and a higher magnetic field value. Each sector coil element has legs for leading a current in different directions. With this azimuthally varying field a high flutter amplitude can be obtained and hence an optimum beam focussing can be obtained.

The magnetic structure according to the invention preferably further comprises a ferro-magnetic assembly comprising magnetically interconnected portions for guiding a magnetic flux from each of the sector coil elements.

The present invention is in particular related to a magnet structure for an isochronous compact cyclotron for accelerating charged particles, configured for generating a magnetic field across an acceleration region, said magnetic field being perpendicular to a median plane of said acceleration region, characterised in that said magnetic structure is further comprising a series of three or more superconducting sector coil elements located on top and below said acceleration region, each sector coil element having legs for leading a current in different directions, said sector coil elements being configured for varying azimuthally said magnetic field between a lower magnetic field value and a higher magnetic field value.

Advantageously, with such magnetic structure according to the invention a compact cyclotron can be built by using a high azimuthally averaged magnetic field while keeping a high flutter amplitude so that an optimum vertical focussing of the accelerated beam is obtained.

Preferably, the sector coil elements have each an outbound leg for leading a current in an outwards direction out of said acceleration region, a inbound leg for leading a current in an inwards direction in said acceleration region, and an external return leg at the periphery of said acceleration region for leading a current from said outbound leg to said inbound leg.

Preferably, each of the sector coil element further comprises an internal return leg for leading a current from said inbound leg to said outbound leg of the same sector coil element, thereby forming a closed sector coil.

Alternatively, each of the sector coil elements can comprise an internal return leg for leading a current from a said inbound leg to an outbound leg of a adjacent sector coil, thereby forming a clover-leaf shaped closed coil.

Preferably, the azimuthally-averaged magnetic field in the cyclotron is larger than 4 T.

Preferably, the difference between said higher and said lower magnetic field value is in the range between 2 and 5 T.

Preferably, the magnet structure comprises four superconducting sector coil elements positioned below the median plane and four superconducting sector coils positioned above the median plane.

Preferably, said inbound legs and said outbound legs are linear and oriented radially.

Preferably, said inbound legs and said outbound legs have a spiral shape.

Preferably, said magnet structure further comprises one or more superconducting annular coils encompassing said acceleration region for increasing said magnetic field.

Preferably, said magnetic structure further comprises ferro-magnetic poles located either inside said sector coil elements or outside said sector coil elements, thereby increasing the azimuthal variation of said magnetic field.

Preferably, said magnetic structure further comprises a ferro-magnetic return yoke.

The present invention also relates to an isochronous cyclotron comprising a magnetic structure according to the invention. The cyclotron is preferably configured for producing a beam having an energy adapted for use in particle therapy. Advantageously, the cyclotron comprises an ion source for bringing ions in the central region of the cyclotron. In this way, the ions can start their first turn in the cyclotron at a radius that is equal or less than 10% of the extraction radius of the cyclotron.

The present invention further relates to the use of said magnet structure for obtaining an isochronous compact cyclotron.

SHORT DESCRIPTION OF THE DRAWINGS

These and further aspects of the invention will be explained in greater detail by way of example and with reference to the accompanying drawings in which:

FIGS. 7a and 7b are top views of two further embodiments according to the invention where central coils are installed in addition to sector coil elements.

The figures are not drawn to scale. Generally, identical components are denoted by the same reference numerals in the figures.

DETAILED DESCRIPTION OF THE INVENTION

A magnet structure for an isochronous compact cyclotron comprises a superconducting coil assembly and a ferro-magnetic assembly. The ferro-magnetic assembly comprises magnetically interconnected portions for guiding a magnetic flux. Portions of the ferro-magnetic assembly can for example be magnetically interconnected by having portions that touch each other or, in another example, the ferro-magnetic assembly can be made from a single piece, or portions can be interconnected by any other magnetic coupling. The magnetic structure further comprises a cavity (i.e. an opening or an area or a gap) forming an acceleration region.

The magnet structure 1 according to the invention is designed for generating a magnetic field which is perpendicular to the median plane X,Y of the accelerator. The cavity, e.g. a cylindrical cavity, forming a circular acceleration region is located in the median plane of the cyclotron. The magnetic structure 1 according to the invention comprises a superconducting coil assembly comprising a series of three or more sector coil elements each having legs for leading a current in different directions. The sector coils are located on top and below the acceleration region. Those sector coils elements 20 are configured for varying azimuthally the magnetic field between a lower magnetic field value and a higher magnetic field value. With the magnetically interconnected portions of the ferro-magnetic assembly, a magnetic flux from each of the sector coil elements 20 is guided with an integrated ferro-magnetic structure.

The azimuthally variation of the magnetic field with the sector coils elements 20, as discussed above, is understood in the usual sense, i.e. azimuthal is in respect of a central axis of the magnetic structure. The central axis is perpendicular to the median plane and goes through the centre of the cyclotron. In other words, an ion being accelerated in the cyclotron will observe alternating a magnetic field with the lower magnetic field value and a magnetic field with the higher magnetic field value.

A number of embodiments according to the invention are described below, focusing on variations of the superconducting coil assembly according to the invention.

Figure 1B:
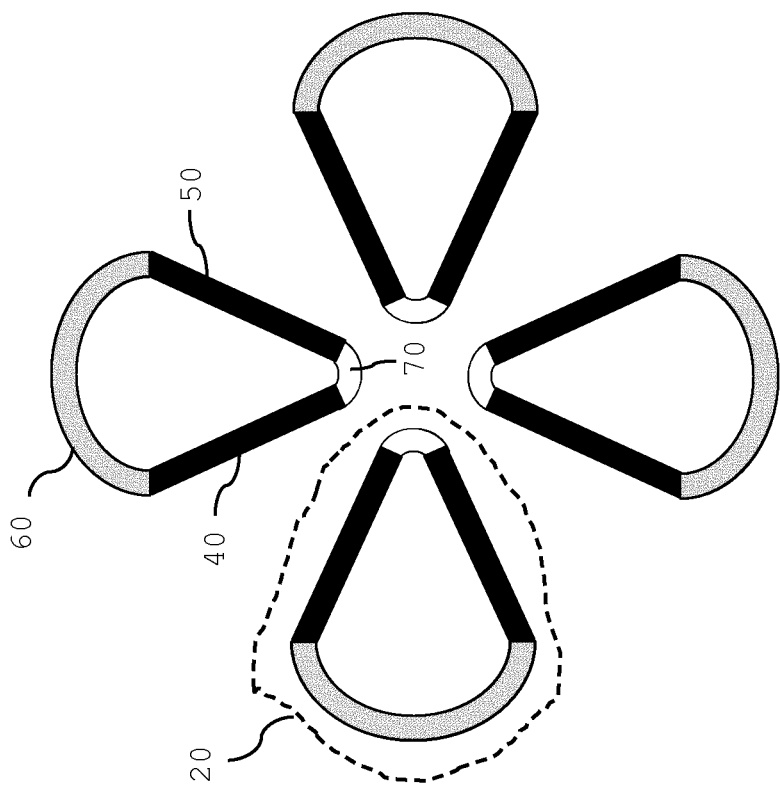
FIGS. 1a and 1b are top views of a first and second embodiments of the invention where four sector coils are assembled as a clover-leaf and as four distinct sectors, respectively.
Figure 1A:
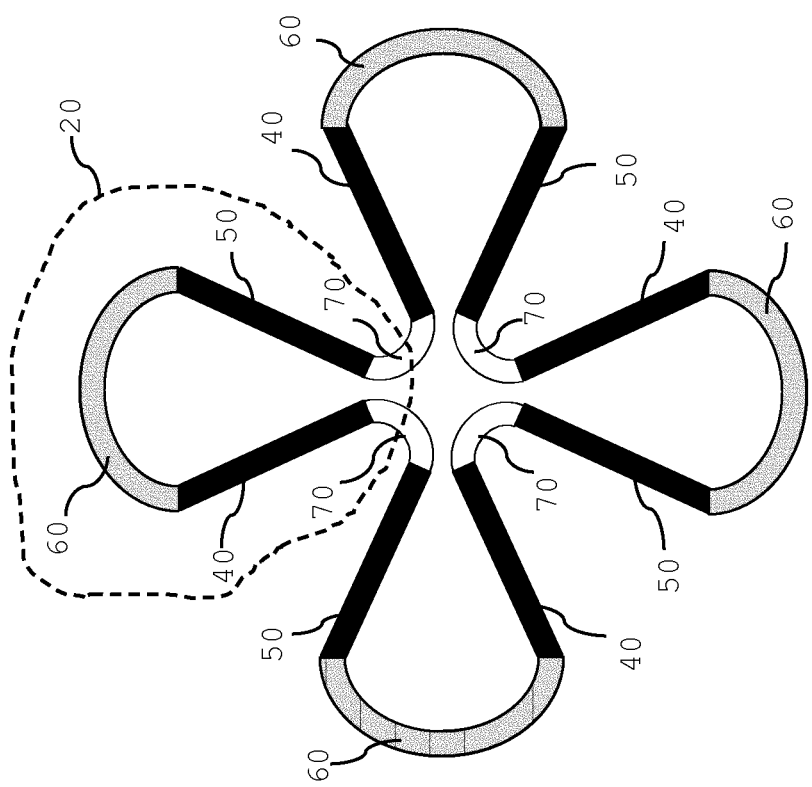
Figure 2A:
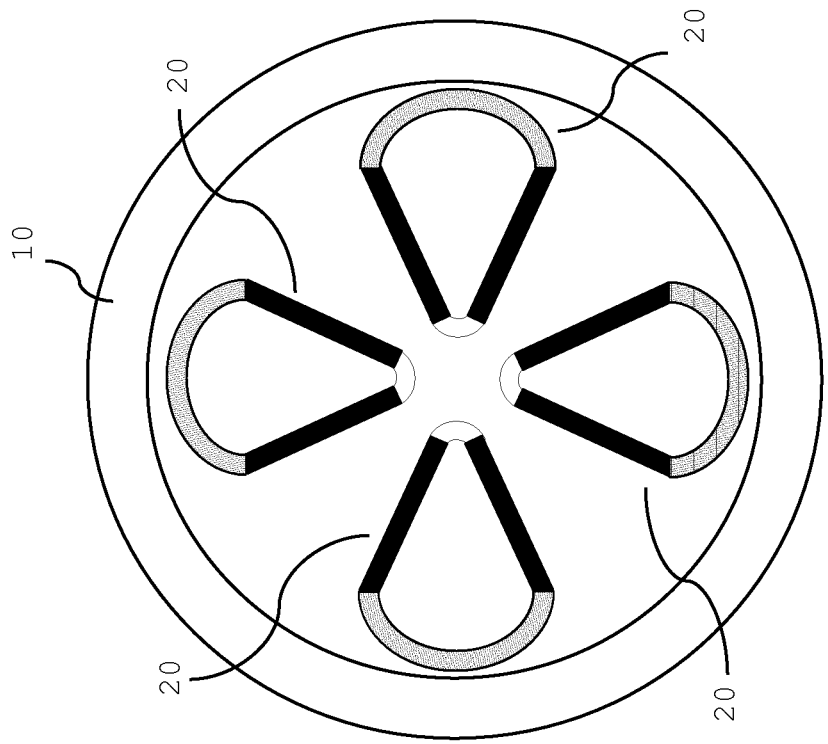
FIGS. 2a and 2b are top views corresponding to FIGS. 1a and 1b, with the addition of a superconducting annular coil encompassing the sector coils.

A magnet structure according to a first embodiment of the invention comprises a superconducting coil assembly as represented on FIGS. 1a and 2a. It is characterized in that the superconducting coil assembly comprises one type of superconducting coils, namely a plurality of superconducting sector coil elements. The magnet structure represented on FIGS. 1a and 2a comprises a plurality of and preferably four sector coil elements 20 each comprising an outbound leg 40, an inbound leg 50, and an external return leg 60 for leading a current from the outbound leg 40 back to the inbound leg 50. In addition, an internal return leg 70 is provided for leading a current from one inbound leg 50 to an outbound leg 40 of an adjacent sector coil element 20, thereby forming a single clover-leaf shaped closed coil. As is well known, these coils may be formed from a plurality of individual leads wound along parallel paths.

In a preferred embodiment, the magnetic structure comprises two series of four sector coil elements. A first series of four sector coil elements 20 forming a clover-leaf shaped closed coil is installed on top of the acceleration region and a second series of four sector coil elements 20 forming a second clover-leaf shaped closed coil is installed below the acceleration region in a symmetric way. With these clover-leaf shaped coils an azimuthally varying magnetic field is created.

Figure 2B:
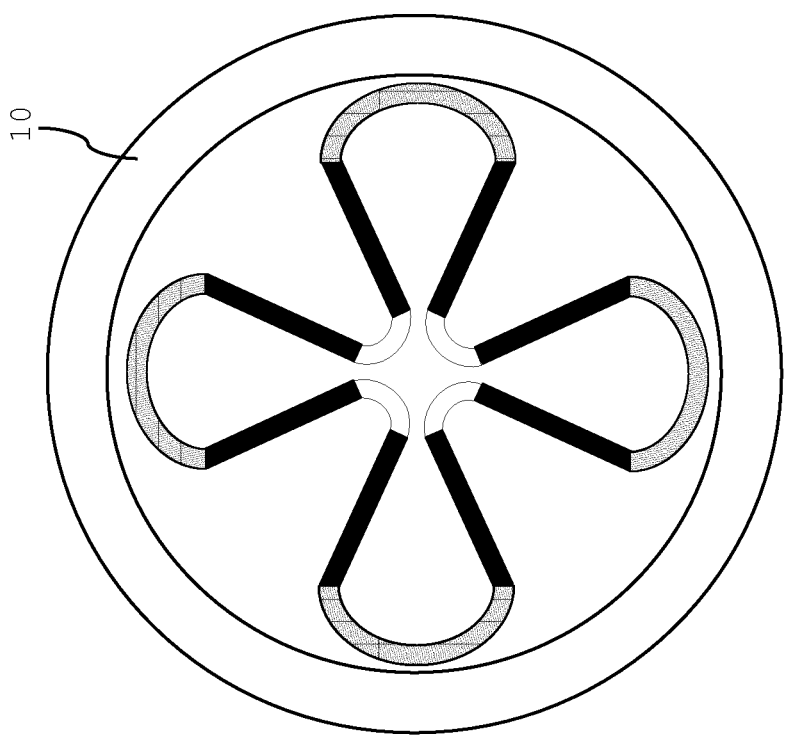

As an alternative, represented on FIGS. 1b and 2b, the internal return legs 70 may be disposed for leading a current from an inbound leg 50 to the outbound leg 40 of the same coil element 20, thereby forming a plurality of closed sector coils.

The sector coil elements 20 shown in FIG. 1a and FIG. 1b are configured for varying azimuthally the magnetic field between a lower magnetic field value and a higher magnetic field value. For example, the lower magnetic field value is 3 Tesla and the higher magnetic field value is 7 Tesla.

Figure 3:
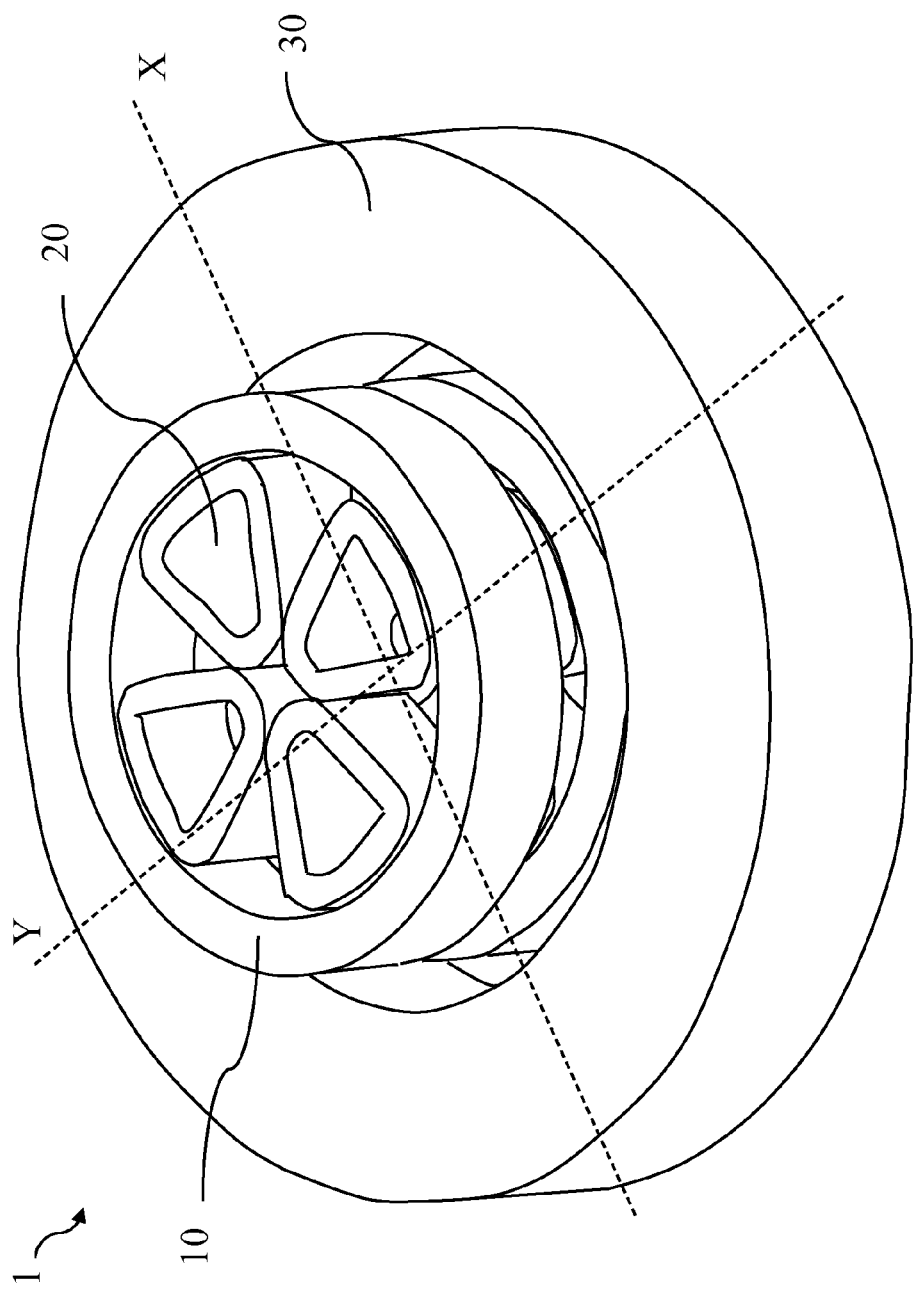
FIG. 3 is a three-dimensional schematic representation of a magnetic structure of a superconducting isochronous cyclotron according to the invention.
Figure 4:
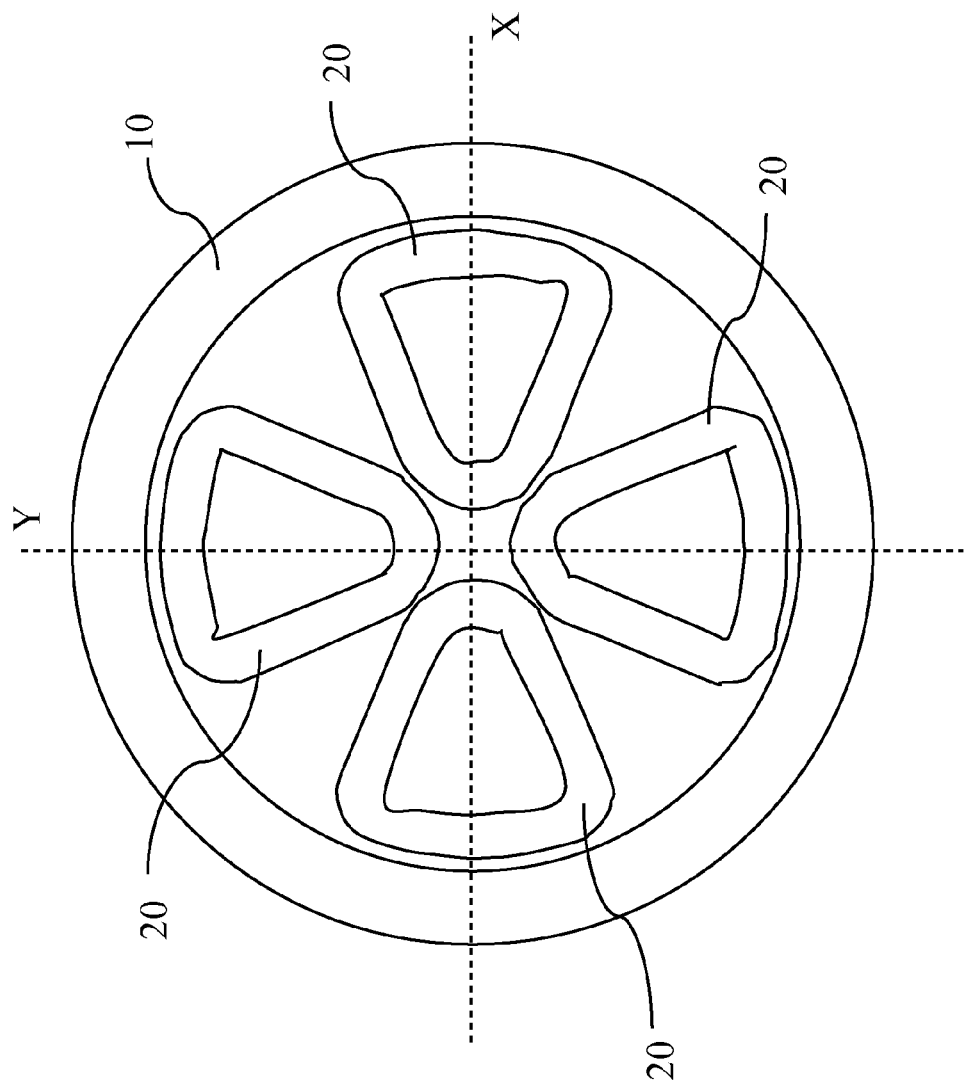
FIG. 4 shows a top view of a schematic representation of a magnetic configuration for a superconducting cyclotron according to the invention.

The magnet structure according to a second embodiment of the invention represented on FIGS. 2, 3 and 4 is characterized in that the superconducting coil assembly comprises two types of superconducting coils. A first type of coils is a set of two superconducting annular coils 10 that are positioned around the circular acceleration region of the accelerator. The two coils 10 are spaced apart and located in a symmetric way on each side of the median plane. The acceleration region is located in the space between the two coils.

A second type of coils used are the superconducting sector coil elements 20 described above in relation to FIG. 1a or 1b. A series of superconducting sector coil elements 20 are installed on top and below the circular acceleration region and are located within the inner diameter of the coils 10. Three or more sector coil elements 20 can be installed in a symmetric way along each side of the median plane X,Y.

FIGS. 2a and 2b are top views corresponding to FIGS. 1a and 1b, with the addition of a superconducting annular coil 10 encompassing the sector coils.

A typical geometry of the magnetic structure of a superconducting isochronous cyclotron according to the invention is shown in FIG. 3 where two coils 10 and two sets of four sector coil elements 20 are installed.

In this second embodiment, the ferro-magnetic assembly of the superconducting cyclotron according to the invention comprises a ferro-magnetic return yoke 30 which is surrounding the coils (only part of the return yoke is shown in FIG. 3). The return yoke is e.g. made of iron. Such a return yoke can be interpreted as having a number of portions which are magnetically interconnected portions such that the magnetic flux from each of the sector coil elements (20) is guided through an integrated ferro-magnetic structure. Other geometries for a return yoke can also be used, for example a return yoke having lateral openings for providing access for a pump system or a cooling system or an RF system.

In FIG. 4, a schematic representation is given of a section in the median plane X,Y of the magnetic structure of FIG. 3.

The first type of coil, the annular coil 10 provides for a main magnetic field strength across the acceleration region (for example 5 T) and the sector coil elements 20, each provide for an additional field strength (of for example 2 T). The resulting magnetic field is then a magnetic field that is varying azimuthally from a lower magnetic field value to a higher magnetic field value. With the exemplary field strength numbers given for the two types of coils, the resulting magnetic field strength is roughly varying azimuthally between 3 T and 7 T. In other words, the sector coils play the role of the poles with hills and valleys of a standard cyclotron as discussed in the prior art section. Hence, the azimuthally varying magnetic field generated by the combined field of the annular coils 10 and the field of the sector coil elements provide for the necessary focusing effect and optimization of the flutter amplitude. The number of superconducting sector coil elements 20 required depends on the energy the accelerator has to provide. For proton energies below 200 MeV, a three sector design can be sufficient but for energies above 200 MeV at least a four sector design is required due to the harmonic 3 resonance effect. By properly selecting the field strength contribution from both the annular coils 10 and the sector coil elements 20, the flutter amplitude can be correctly defined and controlled.

What superconducting coil assembly to select, either one according to the first embodiment or one according to the second embodiment, as described above, will depend on specific design requirements such as the average azimuthal magnetic field that is required. The characteristic part of both embodiments is the presence of the superconducting sector coil elements 20 that provide for the azimuthal field variation between a lower magnetic field value and a higher magnetic field value. With this azimuthal field variation, a flutter amplitude is obtained that allows optimum vertical beam focussing.

Figure 5:
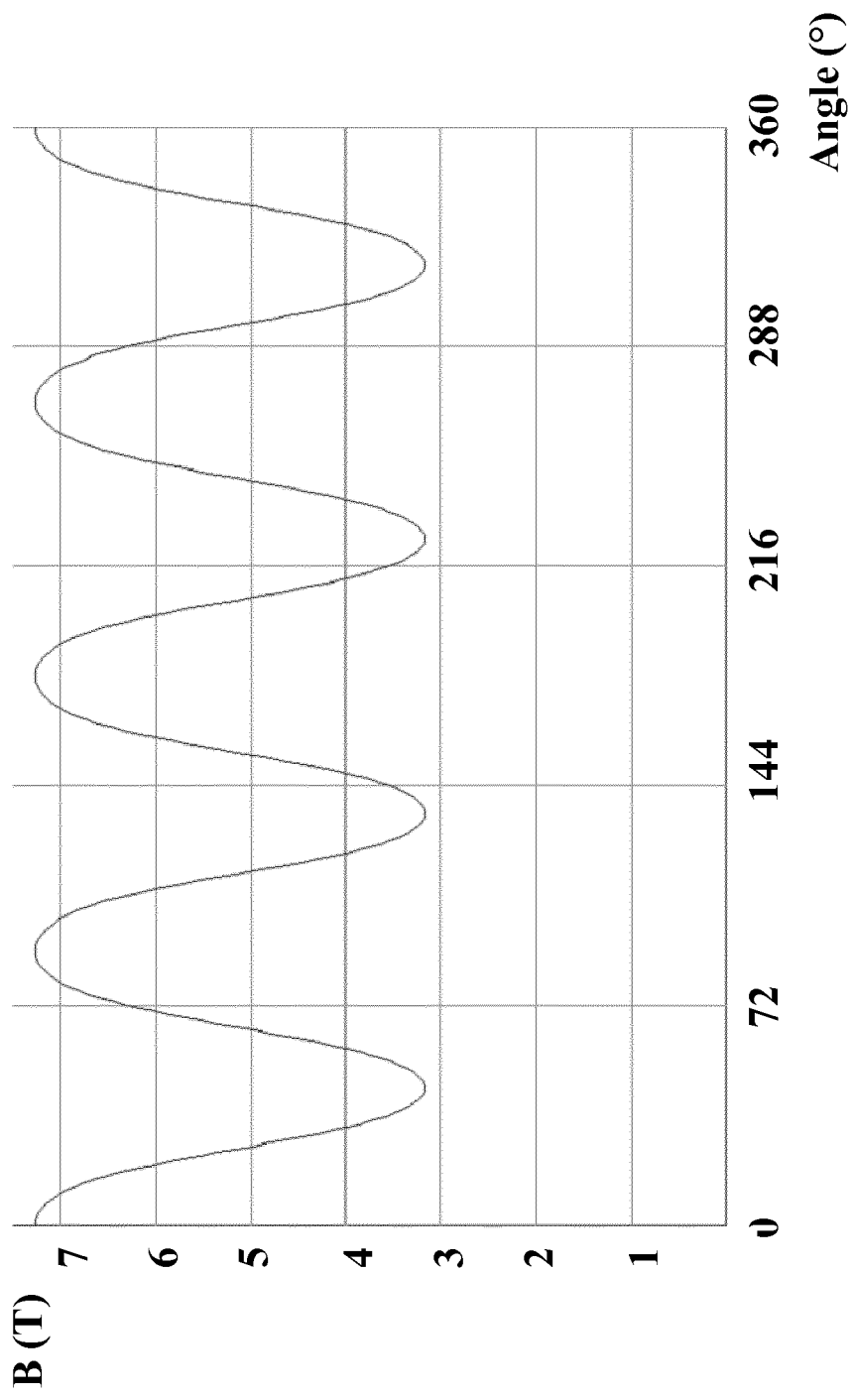
FIG. 5 shows an azimuthally varying averaged magnetic field in a superconducting cyclotron according to the invention.

To illustrate the realization of such an accelerator, a preferred embodiment has been designed and is now further discussed. The magnetic configuration in FIG. 3 is a magnetic structure designed for the exemplary embodiment which is a 250 MeV proton synchronous superconducting cyclotron. This accelerator has an extraction radius of about 50 cm and an outer yoke radius of about 125 cm. This outer radius of the cyclotron has to be compared with the 160 cm outer radius of the prior art superconducting accelerators discussed in the introduction. In this example, the magnetic structure comprises two superconducting coils 10 for generating the main component of the magnetic field. These annular coils 10 induce a magnetic field strength of about 5 T at the centre of the accelerator. This embodiment comprises two sets of four superconducting sector coil elements 20 which, in this example, have a triangular shape as shown in FIG. 4. The triangular shape is formed by the four legs of the sector coil element 20, i.e. the inbound 50 and outbound 40 leg and the internal 70 and external 60 return leg, as shown in FIG. 1*a* and FIG. 1*b*. Each sector coil element 20 provides a field strength of about 2 T. In FIG. 5, the resulting calculated magnetic field strength at the extraction radius is plotted as function of the azimuthal angle. As shown, the magnetic field varies azimuthally from a lower value of about 3 T to a higher value of about 7 T.

Figure 6:
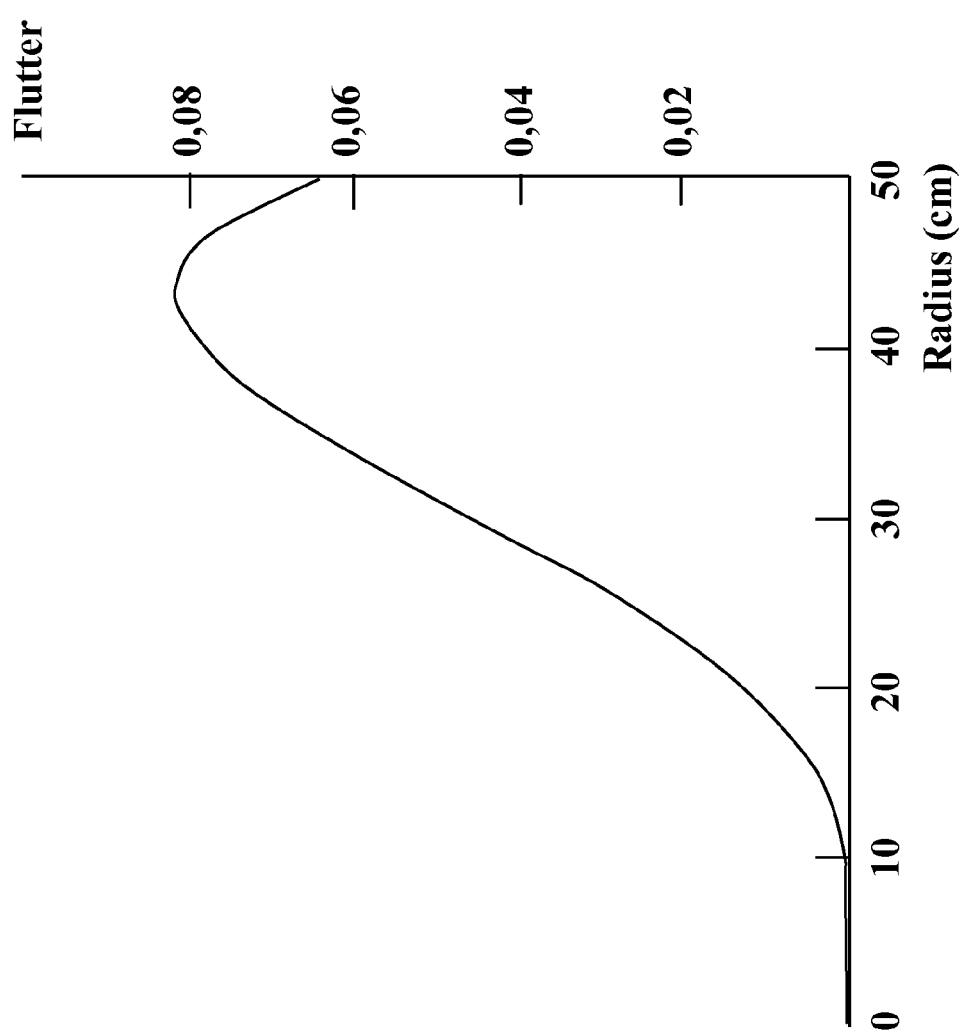
FIG. 6 shows the flutter amplitude as function of radius in a superconducting isochronous cyclotron according to the invention.

In FIG. 6, the calculated flutter amplitude as function of the distance to the centre of the accelerator region, is shown. As shown, satisfactory values for the flutter amplitude are obtained.

The annular coils 10 are enclosed in a cryostat (not shown on FIG. 3) which is filled with liquid helium for cooling the coils. Alternatively, dry cryo-coolers can be used to cool the coils. The two sets of four superconducting sector coils 20 also need to be cooled and in a preferred embodiment the sector coils are cooled using the same cryostat. Alternatively, separate cryostat systems for cooling the annular coils 10 and cooling the sector coils 20 can be used as well.

In the exemplary embodiment according to the invention, the ferro-magnetic assembly does not comprise a pair of poles which means that there is no contribution of the iron to the total magnetic field in the acceleration plane. But, in this embodiment, the ferro-magnetic assembly according to the invention comprises a ferro-magnetic return yoke 30 surrounding the acceleration region as discussed above and shown on FIG. 3.

In a more preferred embodiment, the superconducting sector coil elements 20 have spiral boundaries. By using spiral boundaries the vertical focusing can be further optimized. This spiral shape is obtained by using inbound legs 50 and outbound 40 legs having a spiral shape.

In a further embodiment, pole elements could be provided in order to contribute to or correct the resulting magnetic field in the accelerator. Such ferro-magnetic pole elements are located either inside the sector coil elements 20 or outside the sector coil elements 20, thereby adjusting the magnetic field. In this way, the azimuthal variation of the magnetic field can for example be increased or the isochronous magnetic field can be fine tuned.

The superconducting coil assembly of a third embodiment of a magnetic structure according to the invention is shown in FIGS. 7*a* and 7*b* (top views). When compared to the embodiments of FIG. 1*a* and FIG. 1*b*, in these alternative embodiments, the superconducting coil assembly has in addition to the sector coil elements 20 also central coils 80. Those central coils 80 are located centrally in the acceleration region as shown in FIG. 7*a* and FIG. 7*b*. One central coil 80 is installed below and a second central coil 80 is installed above the acceleration region. These central coils 80 can be operated independently from the sector coil elements 20. In this way, the magnetic field in the centre of the accelerator can be adjusted. These central coils 80 can for example be used to reduce the magnetic field in the centre of the accelerator when a sector coil element configuration of FIG. 1*a* is adopted or they can be used to increase the magnetic field in the centre of the accelerator when a sector coil element configuration of FIG. 1*b* is adopted. In this alternative embodiment, the coil geometry is also symmetric below and above the acceleration region of the accelerator, i.e. a central coil 80 is installed below and above the acceleration region. Preferably, these alternative embodiments also make use of ferro-magnetic pole elements located either inside the sector coil elements 20 or outside the sector coil elements 20, thereby adjusting the magnetic field. The central coils 80 are preferably superconducting coils.

In a further embodiment, the superconducting coil assembly of this third embodiment comprising central coils can also further comprise annular coils 10 configured around the sector coil elements 20 as discussed before and shown in FIGS. 2*a* and 2*b*.

In a further embodiment, a magnetic structure according to the invention is obtained by combining the magnet configurations of the embodiments of FIG. 1*a* and FIG. 1*b*. Such a combined configuration can be made by partly having the legs of the conductors of the sector coil elements 20 being connected as in FIG. 1*a* for forming a clover shaped coil and in addition having part of the conductors of the sector coil elements 20 being connected as in FIG. 1*b* for forming individual closed sector coils. In this way, by adjusting the relative magnetic field contributions from each type of coil configuration the overall magnetic field can be better controlled.

The present invention has been described in terms of specific embodiments, which are illustrative of the invention and are not to be construed as limiting.

Preferably, the magnet structure according to the invention has an azimuthal variation of the magnetic field whereby the difference between the higher and the lower magnetic field value is in the range between 2 and 5 T.

Advantageously, the lower magnetic field value is equal or higher than 1 T.

Although the exemplary embodiment describes an embodiment having an average field of about 5 T, the invention is also applicable for other fields. Practically, the magnetic structure of the invention is applicable for superconducting isochronous cyclotrons having average magnetic fields ranging between 3 T and 10 T. Advantageously, the azimuthally averaged magnetic field value is larger than 3 T. More advantageously, the azimuthally averaged magnetic field value is larger than 4 T.

An isochronous cyclotron comprising a magnetic structure according to the invention can further comprise an ion source for bringing ions in the central region of the cyclotron. The ions will then start their first turn close to the centre of the cyclotron, i.e. the ions will start their first turn in the cyclotron at a radius that is equal or less than 10% of the extraction radius of the cyclotron. The ion source can for example be installed in the central region of the accelerator or there can be means for having an axial entrance opening for bringing ions to the central region.

More generally, it will be appreciated by persons skilled in the art that the present invention is not limited by what has been particularly shown and/or described hereinabove. The invention resides in each and every novel characteristic feature and each and every combination of characteristic features.

Reference numerals in the claims do not limit their protective scope.

Use of the verbs "to comprise", "to include", "to be composed of", or any other variant, as well as their respective conjugations, does not exclude the presence of elements other than those stated.

Use of the article "a", "an" or "the" preceding an element does not exclude the presence of a plurality of such elements.

The invention claimed is:

1. A magnet structure for an isochronous compact cyclotron for generating a magnetic field across an acceleration region and whereby said magnetic field is perpendicular to a median plane of said acceleration region, said magnet structure comprising:
   a superconducting coil assembly,
   a ferro-magnetic assembly for guiding a magnetic flux, and
   a cavity forming said acceleration region, wherein
   said superconducting coil assembly comprises a series of three or more superconducting sector coil elements located on top and below said acceleration region, each sector coil element having legs for leading a current in different directions, said sector coil elements being configured for varying azimuthally said magnetic field between a lower magnetic field value and a higher magnetic field value, and
   said ferro-magnetic assembly comprises magnetically interconnected portions for guiding a magnetic flux from each of said sector coil elements.

2. The magnet structure according to claim 1, wherein each of said sector coil elements has an outbound leg for leading a current in an outwards direction out of said acceleration region, an inbound leg for leading a current in an inwards direction in said acceleration region, and an external return leg at the periphery of said acceleration region for leading a current from said outbound leg to said inbound leg.

3. The magnet structure according to claim 2, wherein each of said sector coil elements further comprises an internal return leg for leading a current from said inbound leg to said outbound leg of the same sector coil element, each sector coil element thereby forming a closed sector coil.

4. The magnet structure according to claim 2, wherein an internal return leg is provided for leading a current from a said inbound leg to an outbound leg of an adjacent sector coil element, the sector coil elements thereby forming a clover-leaf shaped closed coil below and on top of said acceleration region.

5. The magnet structure according to claim 1, wherein the azimuthally-averaged magnetic field in the cyclotron is larger than 4 T.

6. The magnet structure according to claim 1, wherein the difference between said higher and said lower magnetic field value is in the range between 2 and 5 T.

7. The magnet structure according to claim 1, wherein said superconducting coil assembly comprises four superconducting sector coil elements positioned below the median plane and four superconducting sector coil elements positioned above the median plane.

8. The magnet structure according to claim 2, wherein said inbound legs and said outbound legs are linear and oriented radially.

9. The magnet structure according to claim 2, wherein said inbound legs and said outbound legs have a spiral shape.

10. The magnet structure according to claim 1, wherein said superconducting coil assembly further comprises one or more superconducting annular coils encompassing said acceleration region for increasing said magnetic field.

11. The magnet structure according to claim 1, wherein said ferro-magnetic structure comprises ferro-magnetic poles located either inside said sector coil elements or outside said sector coil elements, thereby adjusting said magnetic field.

12. The magnet structure according to claim 1, wherein said ferro-magnetic assembly comprises a ferro-magnetic return yoke.

13. The magnet structure according to claim 1, wherein said magnetic structure further comprises central coils located centrally above and below said acceleration region.

14. The magnet structure according to claim 1, wherein said lower magnetic field value is equal or higher than 1 T.

15. An isochronous cyclotron comprising a magnetic structure according to claim 1.

16. The isochronous cyclotron according to claim 15 further comprising an ion source for bringing ions in the central region of the cyclotron whereby the ions start their first turn in the cyclotron at a radius that is equal or less than 10% of the extraction radius of the cyclotron.

17. The isochronous cyclotron according to claim 15, wherein said cyclotron is configured for producing a charged particle beam having an energy adapted for use in particle therapy.

18. Use of a magnet structure according to claim 1 for obtaining an isochronous compact cyclotron.

19. A magnet structure for an isochronous compact cyclotron for accelerating charged particles, configured for generating a magnetic field across an acceleration region, said magnetic field being perpendicular to a median plane of said acceleration region,
   said magnetic structure is comprising a series of three or more superconducting sector coil elements located on top and below said acceleration region, each sector coil element having legs for leading a current in different directions, said sector coil elements being configured for varying azimuthally said magnetic field between a lower magnetic field value and a higher magnetic field value and each of said sector coil elements has an outbound leg for leading a current in an outwards direction out of said acceleration region, an inbound leg for leading a current in an inwards direction in said acceleration region, and an external return leg at the periphery of said acceleration region for leading a current from said outbound leg to said inbound leg,
   wherein an internal return leg is provided for leading a current from a said inbound leg to an outbound leg of an adjacent sector coil element, the sector coil elements thereby forming a clover-leaf shaped closed coil below and on top of said acceleration region.

20. The magnet structure according to claim 19, wherein said inbound legs and said outbound legs have a spiral shape.

21. The magnet structure according to claim 19, wherein said inbound legs and said outbound legs are linear and oriented radially.

22. The magnet structure according to claim 19, wherein said magnet structure further comprises one or more superconducting annular coils encompassing said acceleration region for increasing said magnetic field.

23. The magnet structure according to claim 19, wherein said magnetic structure further comprises central coils located centrally above and below said acceleration region.

24. Use of a magnet structure according to claim 19 for obtaining an isochronous compact cyclotron.

25. An isochronous cyclotron comprising a magnetic structure according to claim 19.

* * * * *